US012667655B2

(12) United States Patent
Hellhund et al.

(10) Patent No.: US 12,667,655 B2
(45) Date of Patent: Jun. 30, 2026

(54) TUBE CLAMPING ARRANGEMENT FOR A DIALYSIS MACHINE

(71) Applicants: FRESENIUS MEDICAL CARE DEUTSCHLAND GMBH, Bad Homburg (DE); FRESENIUS MEDICAL CARE AG, Bad Homburg (DE)

(72) Inventors: Jonas Hellhund, Frankfurt a. Main (DE); Gerome Newport Fischer, Weberstedt (DE)

(73) Assignees: FRESENIUS MEDICAL CARE DEUTSCHLAND GMBH, Bad Homburg (DE); FRESENIUS MEDICAL CARE AG, Bad Homburg (DE)

( * ) Notice: Subject to any disclaimer, the term of this patent is extended or adjusted under 35 U.S.C. 154(b) by 634 days.

(21) Appl. No.: 18/006,886

(22) PCT Filed: Jul. 22, 2021

(86) PCT No.: PCT/EP2021/070557
§ 371 (c)(1),
(2) Date: Jan. 26, 2023

(87) PCT Pub. No.: WO2022/023169
PCT Pub. Date: Feb. 3, 2022

(65) Prior Publication Data
US 2023/0256152 A1 Aug. 17, 2023

(30) Foreign Application Priority Data
Jul. 28, 2020 (DE) ..................... 10 2020 119 884.1

(51) Int. Cl.
*A61M 1/36* (2006.01)

(52) U.S. Cl.
CPC ......... *A61M 1/367* (2013.01); *A61M 2205/14* (2013.01); *A61M 2205/3317* (2013.01)

(58) Field of Classification Search
CPC .. A61M 2205/0272; A61M 2205/8287; A61M 39/28; A61M 39/284;
(Continued)

(56) References Cited

U.S. PATENT DOCUMENTS 9,067,051 B2    6/2015  Loth et al.
2008/0134750 A1  6/2008  Riley et al.
(Continued)

FOREIGN PATENT DOCUMENTS

DE      102017001744      8/2018
DE      102018214989      4/2019

*Primary Examiner* — Kai H Weng
(74) *Attorney, Agent, or Firm* — Kilyk & Bowersox, P.L.L.C.

(57) ABSTRACT

The present invention relates to a detection arrangement, comprising: an actuation element, which is designed to be moved back and forth between at least one first and one second position; a fastening portion, which is designed such that the actuation element can be brought into contact with a tube; a spring element, which interacts with the actuation element such that the spring element exerts a force on the actuation element in the direction of the second position; a retaining element, which interacts with the actuation element such that the actuation element can be moved into the first position by means of the retaining element; and a control element, which is designed to detect at least one parameter of the actuation element and/or of the retaining element and evaluate same so that the control element, on the basis of this evaluation, provides information about the condition of the detection arrangement.

18 Claims, 6 Drawing Sheets

Figure 1:
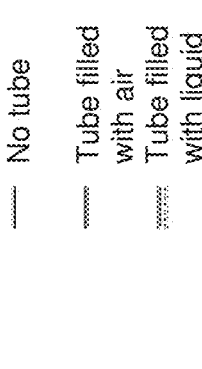
Figure 1:
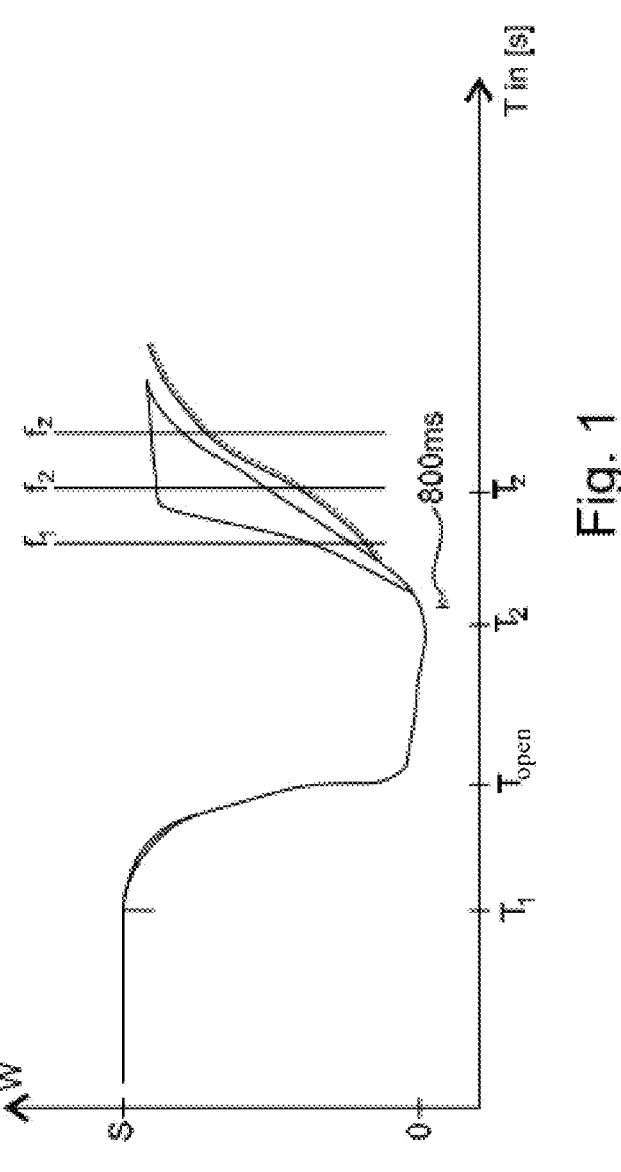

(58) Field of Classification Search
    CPC .. A61M 1/3626; A61M 1/3643; A61M 1/367;
           A61M 2205/14; A61M 2205/3317; F16K
                                                7/045
    See application file for complete search history.

(56)                     References Cited

U.S. PATENT DOCUMENTS

| | | | |
|---|---|---|---|
| 2013/0020237 A1* | 1/2013 | Wilt .................... | A61M 1/1601 |
| | | | 210/85 |
| 2020/0330742 A1* | 10/2020 | Beisser ................ | A61M 39/28 |

* cited by examiner

Control
Signal

Stepper
motor

Holding current
open

Water
content of
the blood

Reciprocal to
viscosity

TREND 1

TREND 2

Treatment
duration

TUBE CLAMPING ARRANGEMENT FOR A DIALYSIS MACHINE

The present invention relates to a detection arrangement comprising an actuation element that is configured to be moved to and fro between a first position and a second position and has a fastening section that is configured such that the actuation element can be brought into contact with a tube.

It is known from the prior art to provide one or more tube clamps in the extracorporeal circuit of a dialysis machine that are suitable for clamping a tube section of the extra-corporeal blood circuit such as the arterial line as required, with blood flowing through said arterial line from the extracorporeal circuit to the patient. It must be ensured prior to the blood treatment, in particular prior to the dialysis treatment, that the respective tube regions have been cor-rectly inserted into tube clamps to ensure patient safety. It is generally possible to provide sensors for this purpose that can detect the presence of a tube; however, this is associated with the disadvantage that the costs and the complexity of the arrangement are thereby increased. Sensors are addition-ally generally also subject to a certain susceptibility to defects.

It is the underlying object of the present invention to further develop a safe detection arrangement of the initially named kind such that it brings about an apparatus and cost effort that is as small as possible.

This object is achieved by a clamp arrangement having the features of claim 1.

A detection arrangement is accordingly configured that has an actuation element that is configured to be moved to and fro between at least one first position and one second position; a fastening section that is configured such that the actuation element can be brought into contact with a tube; a spring element that cooperates with the actuation element such that the spring element exerts a force on the actuation element toward the second position; a retaining element that cooperates with the actuation element such that the actuation element can be moved into the first position by means of the retaining element; and a control element that is configured to detect at least one parameter of the actuation element and/or of the retaining element and to evaluate it such that the control element provides information relating to the state of the detection arrangement on the basis of said evaluation.

In accordance with a further development, the actuation element can be configured as a clamp and the first position can be an open position of the clamp and the second position can be a closed position of the clamp, and the fastening section can be configured as a reception region for the tube.

In other words, a clamping arrangement can be provided comprising:

a. a clamp that is configured to be moved to and fro between an open position and a closed position and has a reception region for a tube;

b. a spring element that cooperates with the clamp such that the spring element exerts a force on the clamp toward the closed position;

c. a retaining element that cooperates with the clamp such that the clamp can be moved into the open position by means of the retaining element; and d. a control element that is configured to detect at least one parameter of the clamp and/or of the retaining element and to evaluate it such that the control element provides information relating to the state of the clamping arrangement on the basis of said evaluation.

The clamping arrangement is suitable, by means of the control element, to determine whether a tube has been inserted or not and/or to recognize whether the tube is filled with liquid or with air.

In accordance with a further development, the actuation element can be configured as a probe finger.

The actuation element can also be designed as a probe finger or as a probe head and not as a clamp. In this respect, the device is not designed to completely compress the tube; it rather has a probe finger that can be brought close to a location at which a tube can be inserted or can be brought into contact with the tube to determine the presence of a tube and further properties of the tube and of the medium therein, as described above for the clamp. A compressing against the tube is to be spoken of here instead of a closing movement, with the movement of the probe finger being able to move in the millimeter range, for instance 0.1 to 10 mm, or in another range, for instance 10 mm to 1 cm. The tube can be compressed and deformed in this process. The actuation element here can be fastened to the tube by means of the fastening section. The probe finger can, for example, be adhered to the tube or can be attached thereto by means of a hose clip. The probe finger here can, however, also be attached to a front side of the dialysis machine, with the tube being able to be inserted in the direct vicinity of the probe finger. The retaining element can also be a spring element, for example a compression spring or a tension spring, in this embodiment. The probe finger can thus always be returned to a predetermined position by means of the spring element. The resetting of the probe finger can also take place in a different purely construction manner, for example while utilizing gravity. In other words, the retaining element can be within the construction design of the detection arrangement.

In accordance with a further development, the spring element can be configured as a magnet, in particular a permanent magnet, an electromagnet, or a polymagnet.

A polymagnet is preferably a magnet that has polarized magnetic pattern areas perpendicular to the surface. Refer-ence is generally made with respect to the disclosure to DE 10 2018 214 989 A1 whose non-restrictive disclosure con-tent is part of the present invention.

When using a polymagnet, a clamping arrangement can be provided that can manage with smaller retaining currents.

The spring element is also configured as a pair of mag-nets, preferably polymagnetized magnets, that is that are formed as a polymagnet. The magnets are here supported or guided such that one of the magnets can execute a movement in the z direction (that is in a direction of the magnets toward one another) and one of the magnets can execute a rotational movement. Alternatively, one of the magnets can be sup-ported or guided such that it can execute a rotational movement and a movement in the z direction. The second magnet is fixed in this embodiment such that neither a rotational movement nor a movement in the z direction is made possible. It is common to both embodiments that the movement of the magnets relative to one another can comprise both a z component and a rotational component. Both magnets have a magnetization pattern imparted; for example a magnetization pattern having 4, 8, or a different number of sectors.

The attraction force of the two magnets with respect to one another provides the closing force of the clamp. The imparted magnetization pattern has the effect that the remaining degree of freedom of the movement of the magnets with respect to one another receives a helical component.

The magnet for which a movement in the z direction is possible can be connected to the clamping element that makes a clamping closed of the tube possible. The magnet for which the rotational movement is possible can be connected to the retaining element. Due to the helical character of the relationship between the z component of the movement of the clamping element and the angular movement of the retaining element, it can be achieved that the retaining forces at the retaining element are much smaller in the open position than the clamping forces in the closed position, that is the closure position.

The insertion of the tube can take place by a manual opening of the clamp by a lever connected to the retaining element. The retaining element, for example an electric motor having an electromagnet, holds the clamp in the open position. Since only small forces are required on the use of a polymagnet to hold the clamp in the open position, the electromagnet can, for example, have smaller dimensions and can thus be lighter overall. In addition, the energy consumption to maintain the open position is smaller. When the retaining current is deactivated, the magnets follow an attraction force toward one another along the helical movement path and the clamping element moves into the closed position.

The spring element is configured to exert a closing force on the clamp. The clamp is thus preloaded to the closed position by means of the spring element. In other words, the spring element can provide a closing force to block the clamp in a currentless state of the retaining element, for example, that is to move it into the closed position. The clamping element blocks the tube in this state.

In contrast, the retaining element is suitable and arranged to exert a force on the clamp acting in the opening direction. The retaining element is preferably configured to move the clamp into the open position and to hold it in this position. The retaining element is suitable, for example, to hold the clamp open against the force of the spring element and/or to open against the force of the spring element starting from a partially or fully closed position.

Provision is preferably made that the control element is configured to activate the retaining element during the closing procedure of the clamp. The parameter value such as the starting current or the current consumption of the retaining element can be detected at or from this time onward and can be used as the basis for the evaluation.

Provision is made in a preferred embodiment of the invention that the spring element has a non-linear force/distance progression, for example on the use of a polymagnet. The force effort for the movement of the spring element, in particular to "load" the spring element, is thus dependent on the position at which the spring element, and thus also the clamp, are located in this embodiment. This non-linearity is in particular sensible when a parameter value is used as the bases at a specific time such as the starting current of the retaining element that depends on the position of the clamp or of a part connected thereto. If the required starting current varies in dependence on the position of the clamp, it is possible to derive the position in which the clamp is located from the starting current and thus to draw a conclusion on whether a tube is in the clamp and, where applicable, whether it is filled with air or blood.

In accordance with a further development, the control element can be configured such that the retaining element is activated during a movement of the actuation element in the direction of the second position to move the actuation element in the direction of the first position.

The present invention relates to the detection arrangement or clamping arrangement with and without an inserted tube. The tube is preferably an extracorporeal blood circuit that preferably has a dialyzer or a hemofilter.

The retaining element is preferably an electric motor, in particular a stepper motor. It cooperates with the clamp such that the electric motor exerts a force on the clamp acting in the open position of the clamp. The retaining element can further comprise an electromagnet that is held in the open position by the electric motor, whereby the clamps is also held in the open position.

Alternatively, the retaining element can be a spring, in particular a compression spring or a tension spring.

In a further embodiment of the invention, a sensor is present to determine the position of the actuation element or of the probe finger or of the clamp. It is conceivable that the clamp has one or more movable clamp blades and that the sensor is arranged such that it can detect the position of at least one clamp blade. A Hall sensor can be considered as the sensor, for example. Every other sensor that is suitable to detect the position of the clamp or of a component of the clamp is, however, also covered by the invention.

In accordance with a further development, the parameter can be the position of the actuation element or of the probe finger and/or of the clamp over the time and/or the parameter is the starting current and/or the current progression over the time of the retaining element.

The parameter that is evaluated by the control element can, for example, be the position of the clamp or of another parameter at a certain point in time. It is also conceivable that the parameter is the time progression of the position of the clamp or the time progression of another parameter.

Provision is made in a further embodiment of the invention that the parameter is the starting current for the retaining element or the current progression over the time of the retaining element. In any case, the position in which the clamp was located at the start of the activation of the retaining element. can be determined from the starting current on a non-linear force/distance progression of the spring element The evaluation is preferably based on the maximum value of the starting current.

In a further possible embodiment, the evaluation by the control element is based on the total current consumption or energy consumption of the retaining element during the opening procedure. It is based on the area below the current/time curve of the retaining element. A conclusion on the position of the clamp can thus also be drawn from the integral of the current progression with a linear force/distance progression.

In other words, the control element is configured to control the retaining element such that the retaining element moves the clamp into the open position or in the direction toward the open position of the clamp. This procedure is preferably executed at a point in time at which the clamp is moved from the open position into the closed position. This closing procedure is interrupted and the clamp is moved back into the open position by means of the retaining element at a specific time, that is after a predetermined duration of the closing procedure. The closing procedure is thus interrupted before the clamp has reached an end position. Depending on whether a tube has been inserted and on which material is present in the tube, the clamp is in a different position of the closing procedure. The starting current of the retaining element can be determined here.

In accordance with a further development, the control element can be configured to control the retaining element such that the actuation element is moved partially or completely into the second position and then partially or completely into the first position.

In accordance with a further development, the control element can be configured such that the partial or complete movement of the actuation element in the direction of the first position and in the direction of the second position can be carried out repeatedly at the same frequency, or at at least two different frequencies, and/or with a frequency sweep.

In other words, the control element can be configured such that the control element controls the retaining element such that the clamp is partially or fully moved into the closed position and then partially or fully into the open position. This procedure can be carried out such that the partial or full opening and closing of the clamp is carried out repeatedly at the same frequency, or at at least two different frequencies, and/or with a frequency sweep.

Conceivable variants not restricting the invention for the detection of the parameter, i.e. measurement variants, are named in the following:

1. One-time opening/closing of the clamp (i.e. actually not regular procedures a) without a sensor and b) with a sensor;
2. Multiple opening/closing of the clamp, i.e. oscillation, at a fixed frequency;
3. Multiple opening/closing of the clamp, i.e. oscillation, at variable frequencies, with at least two different frequencies (a.) and/or one frequency sweep (b.) being present.

1a)

Without the Hall sensor, the clamp additionally has to be opened again in real time after the closing, that is before the reaching of the end position of the clamp—depending on whether a tube had been inserted, the closing procedure has not completely taken place, or the clamp has only undergone one movement pulse in the direction of the closing position. A typical closing procedure is in the order of magnitude of 800 ms. It can preferably be determined by the method whether a tube has been inserted at all and optionally whether gaseous or liquid medium is in the tube.

In this process, a closing procedure is preferably only carried out in part, e.g. until the clamp is still open up to 85% or 90%, for example, when the opening movement is initiated again. A performance of the method is hereby also possible in a manner such that a flow takes place in the tube, e.g. during a priming process, a treatment, or a reinfusion process.

In this respect, the required starting current of the retaining element, for example a motor, can be evaluated. If it is not constant, but rather varies in dependence on the clamp position, if that is the starting current is a function of the clamp position, a conclusion on the position of the clamp can be made via the starting current.

Since the clamping force of the clamp is preferably adapted such that it completely compresses (does not divide, but seals) the tube when the clamping arrangement is switched currentless, information on an insertion state or on the content of a tube in the clamp can preferably be obtained when the clamp opens, closes, and opens again at brief intervals in time before it has fully closed.

The time progression of the closing procedure of the clamp differs here depending on whether a tube has been inserted or not. If there is a tube in the clamp, the closing procedure is slower. The opening procedure thus preferably takes place at the point in time at which the clamp is still not completely closed—depending on the presence/absence of a tube in the clamp—at different positions. Since the tube resistance depends on the medium present in the tube, for example air, blood, or water, and thus differs depending on the medium, the clamp is also at a different position on an interruption of the closing procedure after a predetermined time. The position is here characteristic of the state of the clamping arrangement, that is characteristic of whether there is a tube in the clamp and which medium is filled in it. In other words, a conclusion can be drawn from the different positions of the clamp on whether there is a gas or a liquid in the tube, that is which medium is present in the tube.

The starting current of the retaining element is preferably measured and evaluated prior to the reaching of the closed position of the clamp.

Alternatively, instead of or additionally to the required starting current or its maximum value, the total power consumption on the opening procedure of the clamp effected by the retaining element (area below the current/time curve) can be evaluated. The less widely the clamp has moved into the closed position, the smaller the power consumption (that is the energy consumption) because less "torque×opening distance" has to be overcome, that is less work has to be performed to open the clamp again.

1.b)

In this variant, a sensor such as a Hall sensor is used that determines the position of the clamp and/or of the spring element such as the polymagnetic disk, that is connected to the clamp blade.

No measurement and evaluation of the starting current or of the energy consumption is required on the use of a sensor since the position of the clamp blade can be evaluated directly by the sensor at a point in time or over the time. A measurement and evaluation of the starting current or of the total energy used for an opening procedure can however, be used as additional information and thus a combination of different evaluations can be used.

2.)

The procedure for this generally corresponds to the method in accordance with 1.a). In the simplest embodiment, this procedure additionally permits the state of the tube to be detected, i.e. whether it is filled with gas or liquid.

If the time duration of the closing is selected as brief enough that the clamp only closes by a small amount, a check can be made using the method during an ongoing treatment whether the tube is still inserted. The clamp is here only closed so little that the flow is not restricted or is hardly restricted. This increases patient safety during the treatment.

A procedure using oscillation has a plurality of advantages. A plurality of closing procedures can be evaluated together and the measurement accuracy can thus be increased by repeated measuring. An almost continuous measurement can be made possible by oscillations. Changes at the tube, for instance during the inflow of another medium (priming, reinfusion, air bubbles) over time can thereby be detected. The measurement accuracy can furthermore be increased in that it is not the amplitude of measured values (motor power, clamp position against the time) that is evaluated, but rather a phase position or phase shift in the phase diagram of the oscillation. How the phase position of a specific amplitude level of the motor power follows the signal to open to the motor can thus be evaluated, for example. The evaluation of the phase position of this amplitude level can be possible at a higher sensitivity than the evaluation of the amplitude level itself and can thus deliver more accurate conclusions on the medium in the tube.

Analog to 1.b), this can be detected via a sensor, in particular a Hall sensor or a current sensor.

3.a)

In this process, at least two different frequencies are moved to so that different opening states of the clamp are observed. The "spring constant" of the tube differs depending on whether air or liquid is in the tube from which a different closing state results. However, this "spring constant" of the filled tube depends on the frequency of the oscillation. The contribution of the filling medium in the tube to the "spring constant" of the tube also depends on the frequency. The frequency dependence of different filling media differs, while the frequency dependence of the tube itself, i.e. the contribution of the tub wall independently of the filling medium, does not change when the filling of the tube changes. This property can be used particularly advantageously in that oscillation takes place at two different frequencies and the contribution of the tube alone is deducted. What remains is the contribution of a frequency dependent spring constant that originates only from the medium. An increased measurement accuracy thereby results since the frequency dependence of different filling media differs considerably. A filling of the tube with air or other gaseous media has a behavior that is substantially independent of the frequency. A filling with a medium having a considerably higher mass density, that is additionally not compressible, such as water, dialyzate, saline solution, or blood, in contrast demonstrates a very different, highly frequency dependent behavior. At low frequencies, only a small return force will originate from such a medium, but the return force will become considerably greater at a higher frequency. A conclusion on the properties of the filling medium can be made by a differential evaluation of how much a tube resists an oscillation at two different frequencies, that is at a much higher sensitivity. As a further development, a phase shift of the clamp blade distance can be recognized from the evaluation of the dependence of the distance of the clamp or the clamp blade over the closing time duration, over the position itself, or over the motor power, said phase shift being greater when a less compressible tube has been inserted, e.g. because water is in the tube, not air.

Such an evaluation can take place, for example, by means of a control device that is adapted to carry out the evaluation. Oscillation can take place, for example, at two different frequencies (a higher frequency and a lower frequency) and the control device can be adapted to deduct the contribution of the tube alone so that only the frequency dependent portion is determined. Alternatively or additionally, the control device can be adapted to compare the behavior of an empty tube during oscillation with the behavior of the filled tube (for example during priming) or to form the difference of the corresponding measured values. Further alternatively or additionally, the control device can be adapted to compare the behavior of the filled tube (for example during priming) with the behavior of the tube during a continuous measurement (for example during the treatment) or to form the difference of the corresponding measured values to identify the medium conducted in the tube.

On a use of at least two frequencies, a further evaluation option can additionally or alternatively be added. In this respect, a control signal of the retaining element, for example a stepper motor, can be switched at a first and second frequency. In addition, the duration up to which the specified current value is reached is detected.

Figure 5:
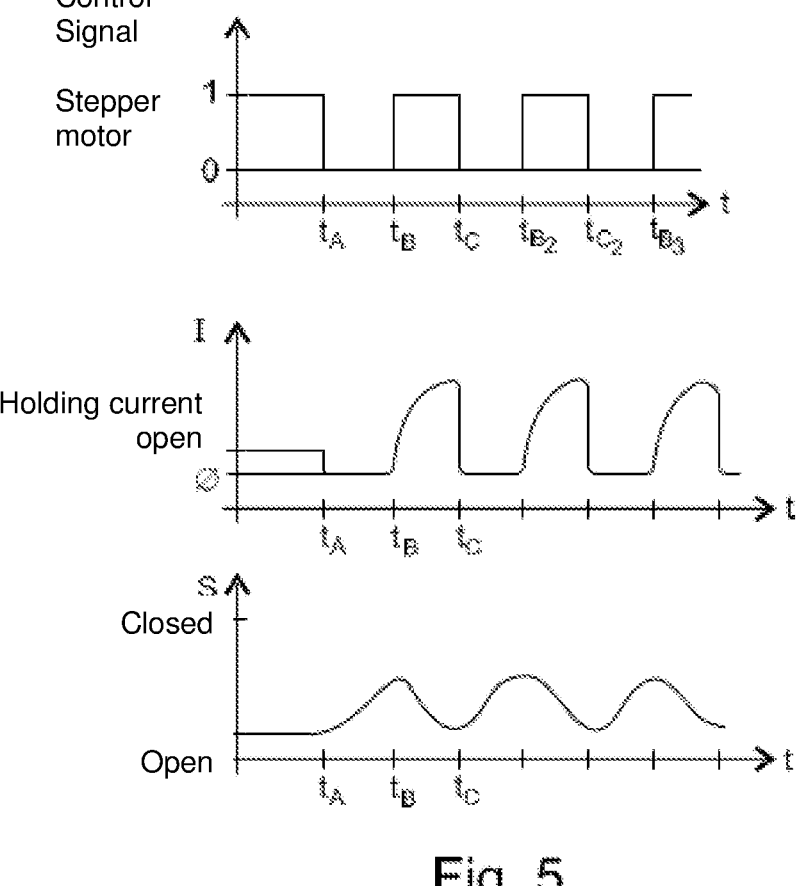

The difference that results between the duration up to the reaching of the specified current value between the frequencies, for example the first and second frequency, provides information on the viscosity of the medium present in the tube. An exemplary relationship between the control signal and the reaching of a specific current value is shown in FIG. 5. The frequency here can, as shown in FIG. 5, be set as so small that a distance change at the clamp cannot yet be measured or can only be unnoticeably measured.

It is equally conceivable to change the control signal from the first frequency to the second frequency in the manner of a ramp. In such a procedure, called a sweep, the frequency is preferably varied, with it changing continuously in one direction, for example from a first lower frequency to a second higher frequency or vice versa. In this case of a sweep, the control signal continuously runs through the frequencies between the first frequency and the second frequency and is thus not only restricted to the first frequency and/or the second frequency.

In addition, a conclusion can thus also be drawn on the tube material, e.g. whether it is PVC or Biofine (PP).

Analog to 1.b), this can be detected via a sensor, in particular a Hall sensor or a current sensor.

3.b)

This method is a further development of the procedure 3.a), with the measurement accuracy generally being increased. Differences can thereby also be recognized depending on whether a priming fluid (saline solution) or blood is in the line. In addition, blood properties can here also be recognized (e.g. differences in the hematocrit. Analog to 1.b), this can additionally be detected via a Hall sensor or a current sensor.

A polymagnet is used as the magnet in an embodiment. However, every other type of magnet can also be used, for example a magnet from neodymium in the form of an induction disk or a ring magnet. In the embodiment using a polymagnet, the characteristic of the starting current results in dependence on the position of the clamp from the dependence on the angular position of the polymagnet: if the clamp is opened wide or fully closed; is a high starting current necessary since a high attraction of the polymagnet is present here. If the clamp is in a middle position, a smaller starting current is required since there is less attraction by the polymagnet. If the clamp is in a still further open position, an even smaller starting current is required since the attraction by the polymagnet is even smaller.

The level of the required starting current can be used as the evaluation parameter by the use of a frequency sweep. Alternatively or additionally, the duration between the current signal and the reaching of a certain specified current value can be used as the evaluation parameter. It can be used for an evaluation of the phase shift.

If the tube is filled with a medium that has a first viscosity that is higher than the viscosity of a second medium, the duration between the current signal and the reaching of the specified current value relative to the second medium is longer. The viscosity of blood, for example, is higher than the viscosity of the dialysis fluid. If the specified current value can be reached fast, that is within a specified time period, a conclusion can be drawn that there is water in the tube system.

On a use of a frequency sweep, a further evaluation option can additionally or alternatively be added. In this respect, a control signal of the retaining element, for example a stepper motor, can be switched at a first and second frequency or at a plurality of different frequencies. In addition, the duration up to which the specified current value is reached is detected.

The difference that results between the duration up to the reaching of the specified current between the frequencies, for example the first and second frequency, provides information on the viscosity of the medium present in the tube. An exemplary relationship between the control signal and the reaching of a specific current value is shown in FIG. 5. The frequency here can, as shown in FIG. 5, be set as so small that a distance change at the clamp cannot yet be measured or can only be unnoticeably measured.

When running through a frequency sweep, a ramp of different frequencies is run through consecutively. In other words, an oscillation begins at a first predetermined limit frequency, is then varied, and then reaches a second predetermined limit frequency.

Frequencies between the two limit frequencies are therefore adopted. In a variant of the invention with the use of a frequency sweep, the frequency dependent response behavior of the tube and of the medium can particularly advantageously be determined. Depending on the composition of the medium in the tube, different frequency dependent characteristic behaviors can be displayed. Characteristic frequency dependent behaviors and a response of the medium to oscillation stimulation can be determined over a wider frequency range by using a frequency sweep.

A medium having a relatively high viscosity (blood) thus damps more at a high frequency than at a low frequency. The characteristic resulting from the comparison at different frequencies is characteristic for the medium in the tube. Since a conclusion on the medium in the tube can be drawn from this evaluation, a conclusion can thus be drawn on different phases of the dialysis treatment. A conclusion can be drawn, for example, on when a change is made from the phase of the liquid removal from the blood into the phase in which liquid is withdrawn from the tissue. The viscosity of the blood increases over the duration of the treatment.

An additional or alternative evaluation can take place independently of the use of a polymagnet. If the clamp is largely or fully closed and there is no tube in the clamp, a high starting current is required since there is no support by a return force of the tube. If the clamp is largely or fully closed and if a tube filled with air or another gas is present in the clamp, a medium starting current is required since there is support for the opening movement by the return force of the tube. If the clamp is largely or fully closed and if a tube filled with blood or with another liquid is present in the clamp, a smaller starting current is required since there is support for the opening movement by the return force of the tube and the blood pressure or liquid pressure in the tube.

This applies analogously to different positions, with the integral of the power consumption also being available here over time as redundant information.

Different geometries of clamps are conceivable in connection with the invention. A narrow edge of the clamp blade of the clamp can thus contact the tube, similar to an edge, or can contact an area, similar to a pipe wrench or clamping jaws of a disk brake. In other words, the clamp blade of the clamp can approximately have a linear contact with the tube.

The actuation element can also be designed as a probe finger or as a probe head and not as a clamp. In this respect, the device is not designed to completely compress the tube; it rather has a probe finger that can be brought close to a location at which a tube can be inserted or can be brought into contact with the tube to determine the presence of a tube and further properties of the tube and of the medium therein, as described above for the clamp. A compressing against the tube is to be spoken of here instead of a closing movement, with the movement of the probe finger being able to move in the millimeter range, for instance 0.1 to 10 mm, or in another range, for instance 10 mm to 1 cm. The tube can be compressed and deformed in this process. The actuation element here can be fastened to the tube by means of the fastening section. The probe finger can, for example, be adhered to the tube or can be attached thereto by means of a hose clip. The probe finger here can, however, also be attached to a front side of the dialysis machine, with the tube being able to be inserted in the direct vicinity of the probe finger. The retaining element can also be a spring element, for example a compression spring or a tension spring, in this embodiment. The probe finger can thus always be returned to a predetermined position by means of the spring element. The resetting of the probe finger can also take place in a different purely construction manner, for example while utilizing gravity. In other words, the retaining element can be within the construction design of the detection arrangement.

The present invention further relates to a dialysis machine that is configured to be equipped with a tube system comprising at least one blood tube or that is equipped with such a tube system (extracorporeal circuit), with the dialysis machine having at least one detection arrangement or a clamping arrangement in accordance with one of the claims 1 to 11. The invention further relates to the use of a detection arrangement or a clamping arrangement in accordance with one of the claims 1 to 11 in a dialysis machine.

Finally, the method relates to the operation of a detection arrangement or a clamping arrangement in accordance with one of the claims 1 to 11 for determining the presence of a tube and/or the tube content. The method steps are the steps named in one or more of the claims 1 to 11.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Figure 2:
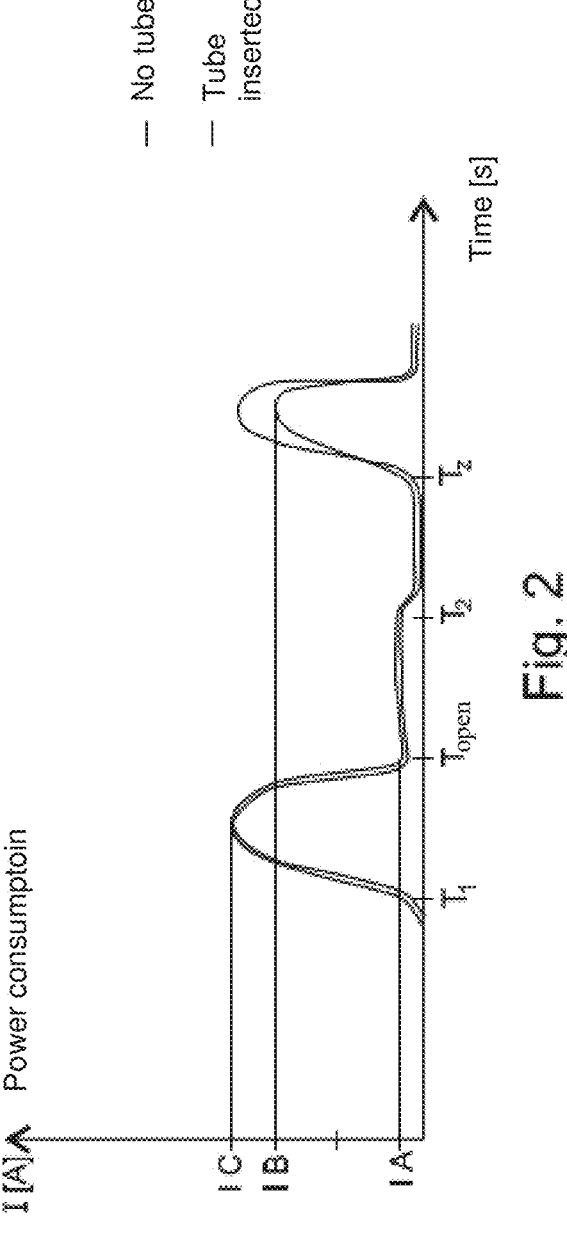
Figure 3:
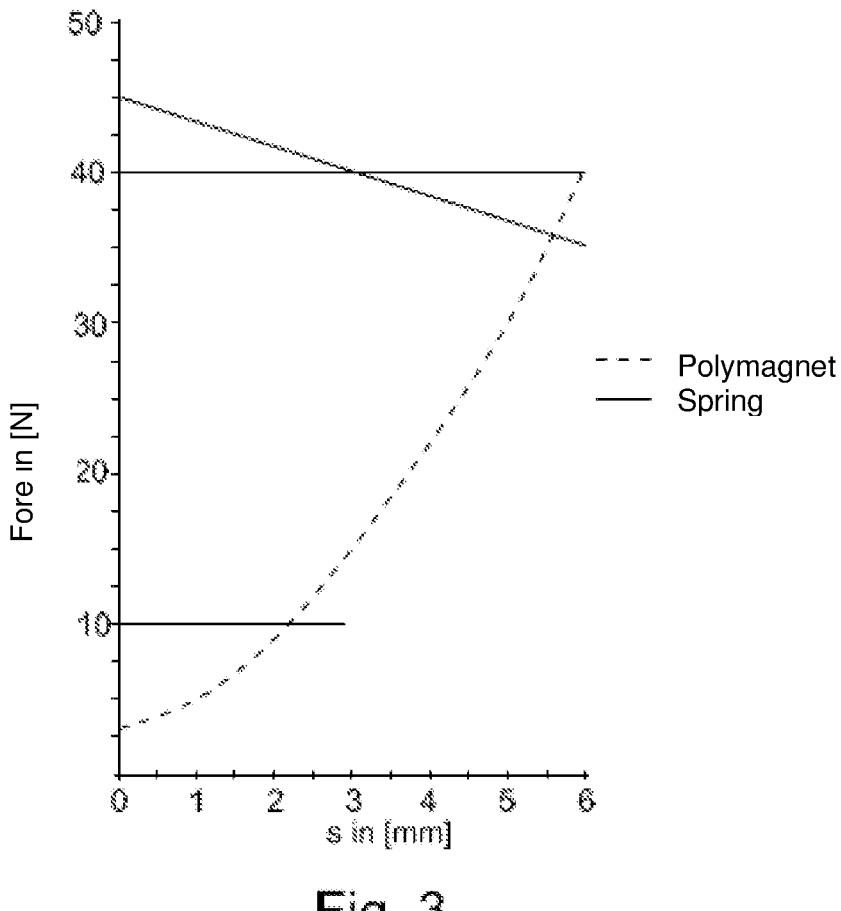
Figure 4:
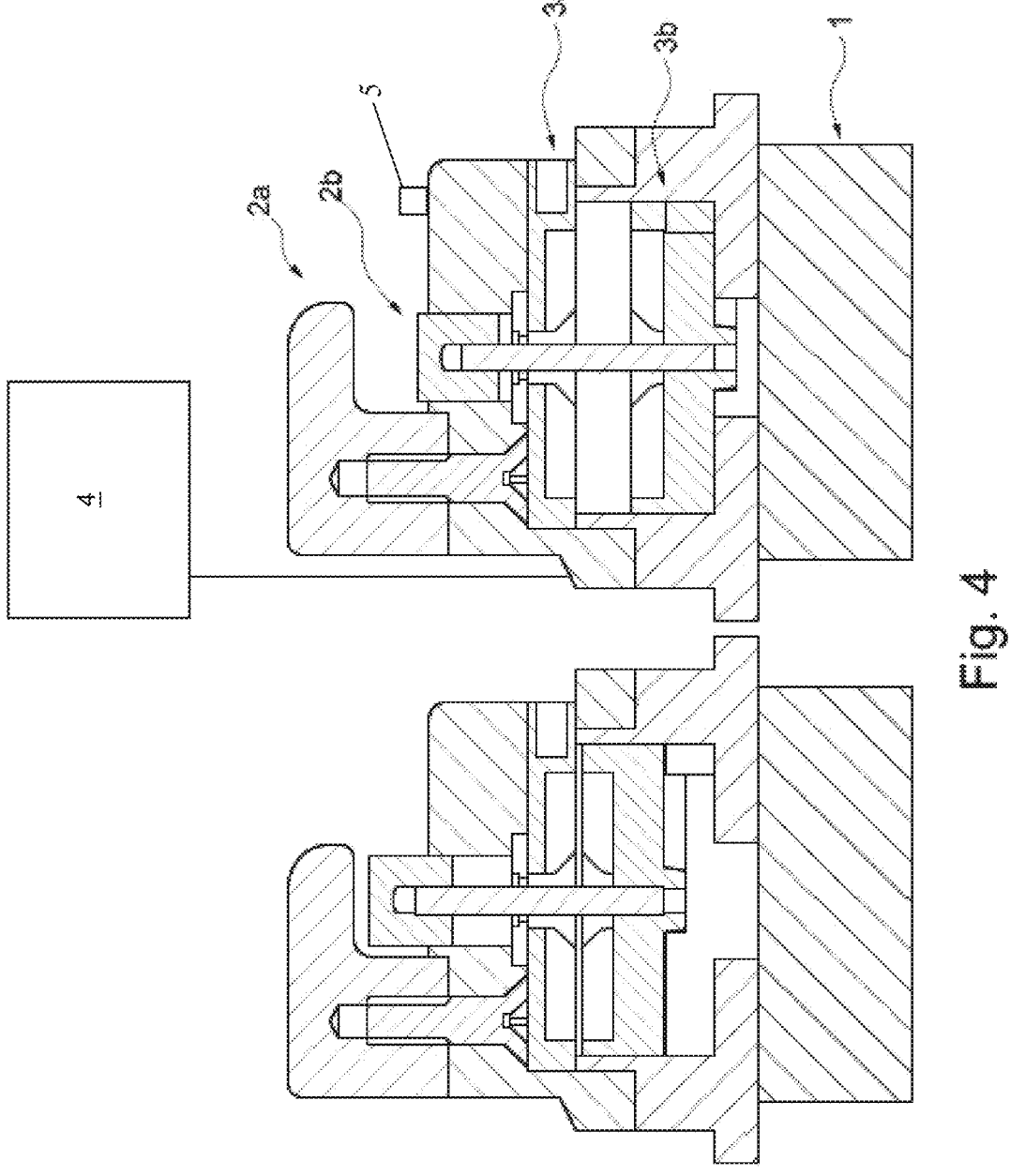
Figure 6:
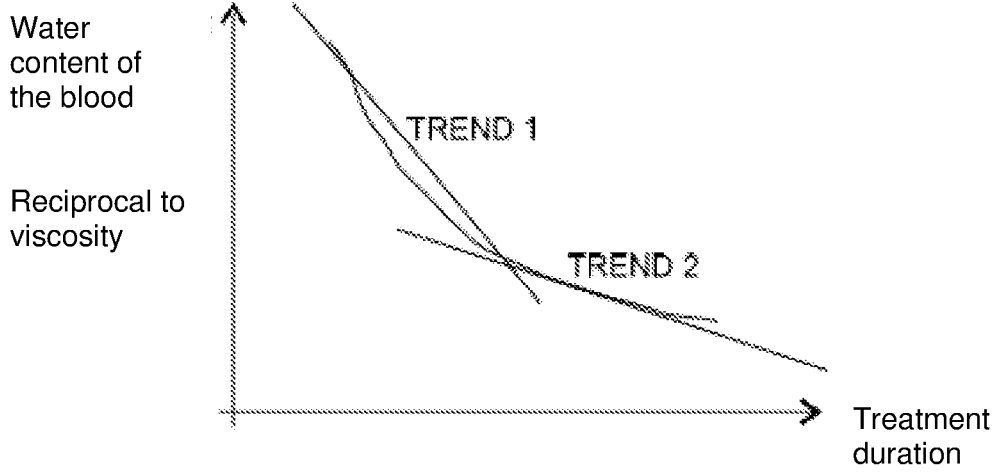

There are shown:

FIG. 1: the time progression of the position of the clamp from closed to open and then to the partially closed state;

FIG. 2: the time progression of the power consumption of the retaining element, with the different times T in accordance with FIG. 1 corresponding to those in accordance with FIG. 2;

FIG. 3: shows an exemplary force/distance progression of a polymagnet in comparison with an alternative spring element;

FIG. 4: a schematic design of an exemplary clamping arrangement;

FIG. 5: an exemplary relationship between the control signal and the reaching of a specific power value; and FIG. 6: an exemplary progression of the viscosity of blood over the treatment duration.

FIG. 1 shows the distance or the position of the clamp blade, i.e. the gripping edge of the clamp over time starting from the closed position W of the clamp.

The time progressions of the position of the clamp blade are shown for three different situations in FIG. 1. FIG. 1 shows the following three variants: A is the time progression without a tube in the clamp; B is the time progression with an air-filled tube in the clamp; and C is the time progression with a liquid-filled tube in the clamp.

FIG. 2 shows the time progression of the power consumption of the stepper motor, i.e. of the retaining element.

FIG. 2 only shows the variants "Tube inserted" and "No tube inserted".

Starting from the coordinate origin, the clamp initially remains closed. The retaining element in the form of a stepper motor is currentless. The closed state S is reached and ensured by a polymagnet. The polymagnet or another spring element is arranged such that the clamp is moved into or held in the closed position by the polymagnet or by the spring element.

The stepper motor is supplied with power at the time $T_1$. The stepper motor exerts a force on the clamp acting in the open position O. This force acts against the force applied by the spring element. The clamp opens, as can be seen from FIG. 1. The clamp has reached its open position at the time $T_{opm}$.

FIG. 2 shows the progression of the power consumption of the retaining element over time and illustrates that a starting current is initially required (between $T_1$ and $T_{open}$) to open the clamp. From the time $T_{open}$ to $T_2$ onward, a retaining force is sufficient to hold the clamp in its open state. In particular the dependence of the required power consumption on the position of the clamp is illustrated in FIG. 2. Here, the power value $I_A$ shows the value required for the maintenance of the open position; $I_B$ illustrates the power value that is required to open the clamp when the clamp was not fully closed; and $I_C$ illustrates the power value that is required to open the clamp when the clamp was fully closed.

It further results from FIG. 2 that both the starting current between $T_1$ a $T_{open}$ and the retaining current that is needed to hold the clamp open is identical or largely identical for the variants "Tube inserted" and "No tube inserted". This is due to the fact that the clamp is opened from its completely closed state and is then held in the open position in both cases, i.e. in all three cases, the position of the clamp (first in the closed position and then in the open position) is identical so that the retaining device has to perform the same work to open the clamp and hold it in this position.

The current of the stepper motor is deactivated at the time $T_2$, which has the result that the clamp starts to close due to the force of the spring element.

FIGS. 1 and 2 schematically show the progressions of the position of the clamp and the power consumption of the stepper motor for the three above-named variants from the time $T_2$ onward. The distance between the progressions of the three variants first increase and then decreases, as can in particular be seen from FIG. 1.

If the progression in accordance with FIG. 1 is measured using a Hall sensor or the like, it can be determined from the absolute value of the distance S at a specific point in time or from the time progression of S over T or from a comparison of the absolute value or of the progression with a reference value whether no tube is inserted in the clamp or whether a tube has been inserted in the clamp and whether it is filled with air or with blood. The clamp is closed the most in the variant without a tube at a specific time $T_z$ since no tube counteracts the closing movement. The blood filled tube is closed the least; the distance for the air filled tube is therebetween. If the absolute position of the clamp or of the time progression is measured, a statement can be made on which variant is present without any measurement of the power consumption.

Alternatively, in a further embodiment that manages without a sensor, the position of the clamp can equally be detected.

A preferred embodiment comprises the starting current of the anyway required retaining element, in particular of the stepper motor, being used to check which of the variants is present. As can be seen from FIG. 2, the retaining element has power applied at the time $T_z$ so that the clamp opens again from this time onward, which is not shown in FIG. 1. FIG. 1 schematically illustrates the different time progressions of the variants during the closing procedure, that is the distance covered by the clamp over the time. FIG. 2 shows the starting current resulting from the different progressions on an interruption of the closing procedure at $T_z$.

The starting current differs both in its maximum value and in its progression, as can be seen from FIG. 2. It results from FIG. 2 that both the maximum value of the starting current and the area under the progression of the current over the time is greater for the case that no tube is inserted than for the case that a hose is inserted.

This is due to the fact that the clamp without a tube has to cover a further distance at the closing procedure starting at the time $T_z$ and has to overcome a greater force of the spring element than is a tube is inserted. It can thus be determined from the absolute value of the starting current and from the integral below the progression of the starting current over the time whether a tube is located in the reception region of the clamp or not.

The above-described closing and opening procedures of the clamp can be carried out once or multiple times. On a multiple opening and closing, the frequency can be set in a suitable manner. In FIG. 1, three frequencies are indicated at which the above-named procedure of the partial closing and opening of the clamp is carried out. The frequency here is f1>f2>f3.

FIG. 3 shows an exemplary force/distance progression of a polymagnet in comparison with an alternative spring element having a linear force/distance progression. A conclusion on the position of the clamp can be drawn from the required starting current due to the non-linear force/distance progression.

FIG. 4 shows a schematic design of an exemplary clamping arrangement. The left side here shows the actuation element 2a, 2b of the clamping arrangement in a closed position while the right side shows the actuation element 2a, 2b of the clamping arrangement in an open position. The retaining element 1 is shown schematically by an electric motor. The spring element 3a, 3b is shown as a polymagnet, with the upper element of the polymagnet being the element rotatable by the electric motor and with the lower element of the polymagnet being the element displaced in the z direction on a rotation of the upper element. The clamp is shifted between the open and closed positions by the displacement of the lower element of the polymagnet. In the closed position shown on the left side, the movable element of the clamp is shifted upward and can clamp a tube closed in this position. A control element 4 is in communication with and is configured to control the clamping arrangement. A sensor 5 is for determining the position of the actuation element 2a, 2b.

An exemplary relationship between the control signal and the reaching of a specific current value is shown in FIG. 5. The frequency here can, as shown in FIG. 5, be set as so small that a distance change at the clamp cannot yet be measured or can only be unnoticeably measured.

FIG. 6 shows by way of example the progression of the viscosity of the blood over the progression of a treatment time. The viscosity here increases with the time, with the water content in the blood decreasing over the treatment time.

The invention claimed is:

1. A detection arrangement comprising:
an actuation element that is configured to be moved to and fro between a first position and a second position, the actuation element comprising a fastening section that is configured such that the actuation element is capable of being brought into contact with a tube;

a spring element that cooperates with the actuation element such that the spring element exerts a force on the actuation element toward the second position;

a retaining element that cooperates with the actuation element such that the actuation element is configured to move into the first position by means of the retaining element; and a control element that is configured to:

control the retaining element such that the actuation element is moved partially or completely into the second position and then partially or completely into the first position, oscillate the actuation element at least partially between the first position and the second position by controlling the retaining element, detect at least one parameter of the actuation element and/or of the retaining element, the at least one parameter being an oscillation characteristic, and evaluate the at least one parameter such that the control element provides information relating to a state of the detection arrangement on the basis of said evaluation.

2. The detection arrangement in accordance with claim 1, wherein the actuation element is configured as a clamp and the first position is an open position of the clamp and the second position is a closed position of the clamp, wherein the fastening section is configured as a reception region for a tube.

3. The detection arrangement in accordance with claim 1, wherein the actuation element is configured as a probe finger.

4. The detection arrangement in accordance with claim 1, wherein the spring element is a magnet.

5. The detection arrangement in accordance with claim 1, wherein the spring element has a non-linear force/distance progression.

6. The detection arrangement in accordance with claim 1, wherein the control element is configured to activate the retaining element during a movement of the actuation element in the direction of the second position to move the actuation element in the direction of the first position.

7. The detection arrangement in accordance with claim 1, wherein the retaining element is a spring and/or an electric motor.

8. The detection arrangement in accordance with claim 1, further comprising a sensor for determining the position of the actuation element.

9. The detection arrangement in accordance with claim 1, wherein the at least one parameter is the position of the actuation element over time and/or in that the at least one parameter is the starting current and/or the current progression over time of the retaining element.

10. The detection arrangement in accordance with claim 1, wherein the control element is configured to carry out the oscillation repeatedly at the same frequency or at at least two different frequencies and/or with a frequency sweep.

11. The detection arrangement in accordance with claim 4, wherein the magnet is a permanent magnet, an electromagnet, or a polymagnet.

12. The detection arrangement in accordance with claim 7, wherein the retaining element is the spring and the spring is a tension spring or a compression spring.

13. The detection arrangement in accordance with claim 7, wherein the retaining element is the electric motor and the electric motor is a stepper motor.

14. The detection arrangement in accordance with claim 5, wherein the spring element is a polymagnet, the retaining element is an electric motor, and the at least one parameter is at least one of: the position of the actuation element over time, a starting current of the electric motor, and a current progression over time of the electric motor.

15. The detection arrangement in accordance with claim 1, wherein the control element is configured to detect the at least one parameter without using a sensor.

16. A dialysis machine that is configured to be equipped with a tube system comprising at least one blood tube or that is equipped with such a tube system, wherein the dialysis machine has at least one detection arrangement in accordance with claim 1.

17. A method of using a detection arrangement in accordance with claim 1, the method comprising determining a presence of a tube and/or a tube content of a dialysis machine.

18. A method of operating a detection arrangement in accordance with claim 1, the method comprising determining the presence of a tube and/or the tube content.

* * * * *